(12) United States Patent
Ouyang et al.

(10) Patent No.: US 11,330,973 B2
(45) Date of Patent: May 17, 2022

(54) PORTABLE AND ERGONOMIC ENDOSCOPE WITH DISPOSABLE CANNULA

(71) Applicant: MICRONVISION CORP., Bellevue, WA (US)

(72) Inventors: Xiaolong Ouyang, Bellevue, WA (US); Shih-Ping Wang, Los Altos, CA (US)

(73) Assignee: MicronVision Corp, Bellevue, WA (US)

( * ) Notice: Subject to any disclaimer, the term of this patent is extended or adjusted under 35 U.S.C. 154(b) by 0 days.

(21) Appl. No.: 17/473,587

(22) Filed: Sep. 13, 2021

(65) Prior Publication Data

US 2021/0401277 A1 Dec. 30, 2021

Related U.S. Application Data

(63) Continuation-in-part of application No. 17/362,043, filed on Jun. 29, 2021, and a continuation-in-part of application No. PCT/US2019/036060, filed on Jun. 7, 2019, and a continuation-in-part of application No. 16/363,209, filed on Mar. 25, 2019, and a (Continued)

(51) Int. Cl.
*A61B 1/00* (2006.01)
*A61B 1/04* (2006.01)
*A61B 1/06* (2006.01)

(52) U.S. Cl.
CPC ........ *A61B 1/0638* (2013.01); *A61B 1/00009* (2013.01); *A61B 1/00186* (2013.01); *A61B 1/043* (2013.01); *A61B 1/0676* (2013.01)

(58) Field of Classification Search
CPC .............. A61B 1/0638; A61B 1/00009; A61B 1/00186; A61B 1/043; A61B 1/0676
See application file for complete search history.

(56) References Cited

U.S. PATENT DOCUMENTS

| 5,667,472 A | 9/1997 | Finn et al. |
| 6,211,904 B1 | 4/2001 | Adair et al. |
| (Continued) | | |

FOREIGN PATENT DOCUMENTS

WO 2016137838 9/2016

OTHER PUBLICATIONS

International Search Report and Written Opinion for PCT/US21/050095, dated Dec. 17, 2021.

*Primary Examiner* — Alexandra L Newton
*Assistant Examiner* — Rynae E Boler
(74) *Attorney, Agent, or Firm* — Wissing Miller LLP

(57) ABSTRACT

An endoscopic system includes a single-use portion and a multiple-use portion. The two portions can be mated and un-mated. The single-use portion includes an elongated cannula that has a bendable section near its distal end providing a "steerable" distal tip. The imaging system includes at least two separate cameras and two separate light sources. The camera and light sources are configured to simultaneously image a target object. By employing different illuminations, different filters and manipulating the spectral responses, different characteristics of the target object can be captured. According to some embodiments, a system (Continued)

processor can coordinate the cameras, the light sources and combine the resulting images to display to an operator an enhanced combined image the object.

20 Claims, 15 Drawing Sheets

Related U.S. Application Data continuation-in-part of application No. PCT/US2017/053171, filed on Sep. 25, 2017.

(60) Provisional application No. 63/218,362, filed on Jul. 4, 2021, provisional application No. 63/213,499, filed on Jun. 22, 2021, provisional application No. 63/197,611, filed on Jun. 7, 2021, provisional application No. 63/197,639, filed on Jun. 7, 2021, provisional application No. 63/183,151, filed on May 3, 2021, provisional application No. 63/153,252, filed on Feb. 24, 2021, provisional application No. 63/149,338, filed on Feb. 14, 2021, provisional application No. 63/138,751, filed on Jan. 18, 2021, provisional application No. 63/129,703, filed on Dec. 23, 2020, provisional application No. 63/124,803, filed on Dec. 13, 2020, provisional application No. 63/121,924, filed on Dec. 6, 2020, provisional application No. 63/121,246, filed on Dec. 4, 2020, provisional application No. 63/107,344, filed on Oct. 29, 2020, provisional application No. 63/087,935, filed on Oct. 6, 2020, provisional application No. 63/083,932, filed on Sep. 27, 2020, provisional application No. 63/077,675, filed on Sep. 13, 2020, provisional application No. 63/077,635, filed on Sep. 13, 2020.

(56) References Cited

U.S. PATENT DOCUMENTS

| | | | |
|---|---|---|---|
| 8,361,775 B2 | 1/2013 | Flower | |
| 8,952,312 B2 | 2/2015 | Blanquart et al. | |
| 2005/0264687 A1 | 1/2005 | Murayama | |
| 2006/0052710 A1* | 3/2006 | Miura | A61B 1/043 600/476 |
| 2006/0259124 A1 | 11/2006 | Matsuoka et al. | |
| 2009/0027489 A1* | 1/2009 | Takemura | A61B 1/045 348/E7.085 |
| 2010/0121142 A1* | 5/2010 | OuYang | A61B 1/317 600/109 |
| 2010/0157039 A1 | 6/2010 | Sugai | |
| 2010/0262017 A1* | 10/2010 | Frangioni | B82Y 10/00 600/476 |
| 2011/0009694 A1 | 1/2011 | Schultz et al. | |
| 2011/0112622 A1 | 5/2011 | Phan et al. | |
| 2012/0165916 A1 | 6/2012 | Jordan | |
| 2014/0296866 A1* | 10/2014 | Salman | G02B 23/2461 606/109 |
| 2015/0018622 A1* | 1/2015 | Tesar | A61B 1/05 600/202 |
| 2015/0018710 A1 | 1/2015 | Furlong et al. | |
| 2015/0088001 A1 | 3/2015 | Lindvold et al. | |
| 2015/0297311 A1 | 10/2015 | Tesar | |
| 2016/0367119 A1 | 12/2016 | Ouyang et al. | |
| 2018/0256009 A1 | 9/2018 | Ouyang et al. | |
| 2019/0216325 A1 | 7/2019 | Ouyang | |
| 2019/0223691 A1 | 7/2019 | Takatsuji | |
| 2020/0204776 A1 | 6/2020 | Themelis | |
| 2021/0401277 A1 | 12/2021 | OuYang et al. | |

* cited by examiner

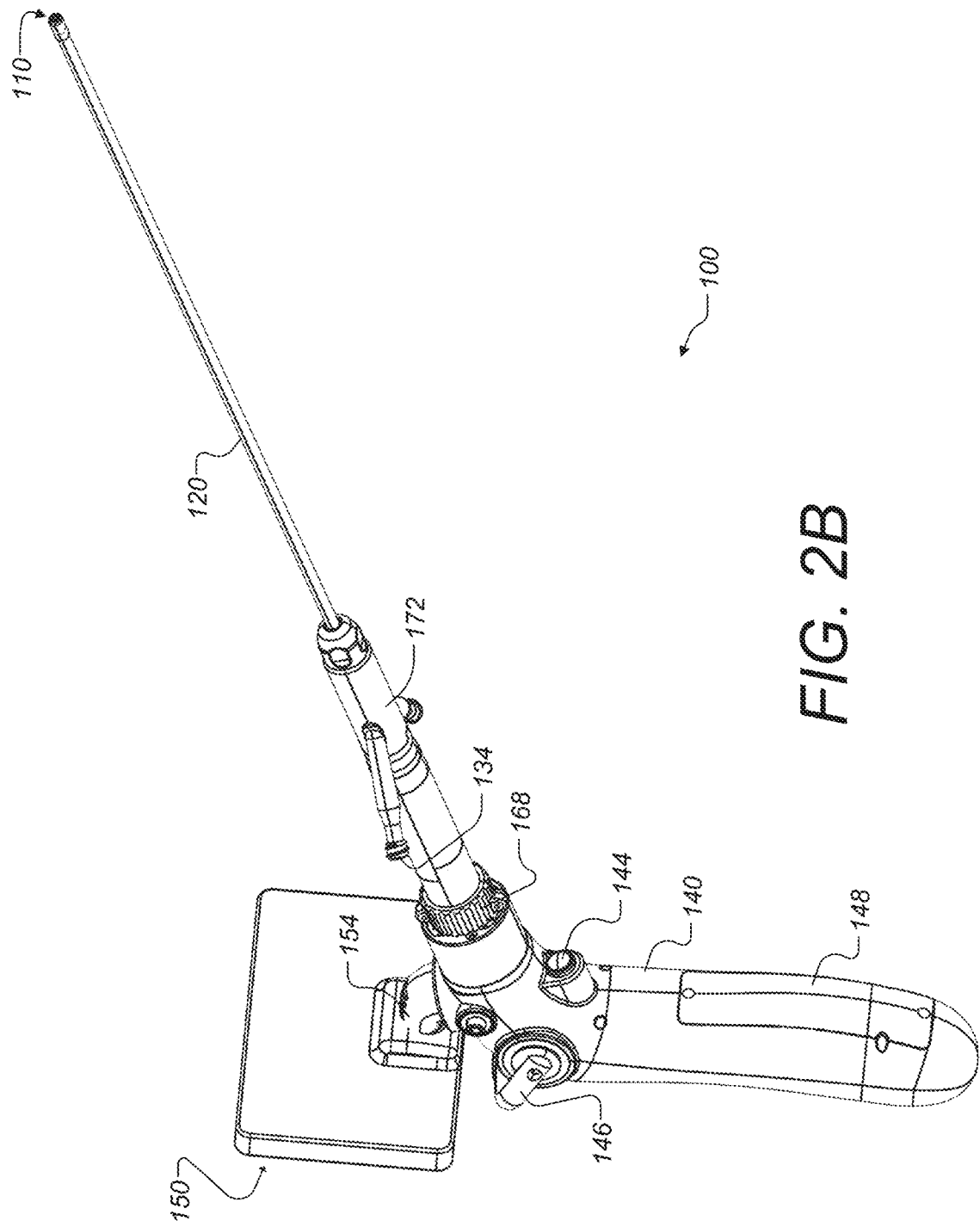

PORTABLE AND ERGONOMIC ENDOSCOPE WITH DISPOSABLE CANNULA

REFERENCE TO RELATED APPLICATIONS

This application is a continuation-in-part of each of: U.S. patent application Ser. No. 17/362,043 filed Jun. 29, 2021; International Patent Appl. No. PCT/US19/36060 filed Jun. 7, 2019; U.S. patent application Ser. No. 16/363,209 filed Mar. 25, 2019 and published as US Pat. Appl. Publ. No. US2019/0216325; and International Patent Appl. No. PCT/US17/53171 filed Sep. 25, 2017.

This application incorporates by reference the entirety of the foregoing patent applications and claims the benefit of the filing date of each of the above-identified patent applications, as well as of the applications that they incorporated by reference, directly or indirectly, and the benefit of which they claim, including U.S. provisional applications, U.S. non-provisional applications, and International applications.

This patent application claims the benefit of and incorporates by reference each of the following provisional applications:

U.S. Prov. Ser. No. 63/218,362 filed Jul. 4, 2021
U.S. Prov. Ser. No. 63/213,499 filed Jun. 22, 2021
U.S. Prov. Ser. No. 63/210,034 filed Jun. 13, 2021
U.S. Prov. Ser. No. 63/197,639 filed Jun. 7, 2021
U.S. Prov. Ser. No. 63/197,611 filed Jun. 7, 2021
U.S. Prov. Ser. No. 63/183,151 filed May 3, 2021;
U.S. Prov. Ser. No. 63/153,252 filed Feb. 24, 2021;
U.S. Prov. Ser. No. 63/149,338 filed Feb. 14, 2021;
U.S. Prov. Ser. No. 63/138,751 filed Jan. 18, 2021;
U.S. Prov. Ser. No. 63/129,703 filed Dec. 23, 2020;
U.S. Prov. Ser. No. 63/124,803 filed Dec. 13, 2020;
U.S. Prov. Ser. No. 63/121,924 filed Dec. 6, 2020;
U.S. Prov. Ser. No. 63/121,246 filed Dec. 4, 2020;
U.S. Prov. Ser. No. 63/107,344 filed Oct. 29, 2020;
U.S. Prov. Ser. No. 63/087,935 filed Oct. 6, 2020;
U.S. Prov. Ser. No. 63/083,932 filed Sep. 27, 2020;
U.S. Prov. Ser. No. 63/077,675 filed Sep. 13, 2020; and
U.S. Prov. Ser. No. 63/077,635 filed Sep. 13, 2020.

This patent application is also related to and incorporates by reference each of the following international, non-provisional and provisional applications:

International Patent Application No. PCT/US17/53171 filed Sep. 25, 2017;
U.S. Pat. No. 8,702,594 Issued Apr. 22, 2014;
U.S. patent application Ser. No. 16/363,209 filed Mar. 25, 2019;
International Patent Application No. PCT/US19/36060 filed Jun. 7, 2019;
U.S. patent application Ser. No. 16/972,989 filed Dec. 7, 2020;
U.S. Prov. Ser. No. 62/816,366 filed Mar. 11, 2019;
U.S. Prov. Ser. No. 62/671,445 filed May 15, 2018;
U.S. Prov. Ser. No. 62/654,295 filed Apr. 6, 2018;
U.S. Prov. Ser. No. 62/647,817 filed Mar. 25, 2018;
U.S. Prov. Ser. No. 62/558,818 filed Sep. 14, 2017;
U.S. Prov. Ser. No. 62/550,581 filed Aug. 26, 2017;
U.S. Prov. Ser. No. 62/550,560 filed Aug. 25, 2017;
U.S. Prov. Ser. No. 62/550,188 filed Aug. 25, 2017;
U.S. Prov. Ser. No. 62/502,670 filed May 6, 2017;
U.S. Prov. Ser. No. 62/485,641 filed Apr. 14, 2017;
U.S. Prov. Ser. No. 62/485,454 filed Apr. 14, 2017;
U.S. Prov. Ser. No. 62/429,368 filed Dec. 2, 2016;
U.S. Prov. Ser. No. 62/428,018 filed Nov. 30, 2016;
U.S. Prov. Ser. No. 62/424,381 filed Nov. 18, 2016;
U.S. Prov. Ser. No. 62/423,213 filed Nov. 17, 2016;
U.S. Prov. Ser. No. 62/405,915 filed Oct. 8, 2016;
U.S. Prov. Ser. No. 62/399,712 filed Sep. 26, 2016;
U.S. Prov. Ser. No. 62/399,436 filed Sep. 25, 2016;
U.S. Prov. Ser. No. 62/399,429 filed Sep. 25, 2016;
U.S. Prov. Ser. No. 62/287,901 filed Jan. 28, 2016;
U.S. Prov. Ser. No. 62/279,784 filed Jan. 17, 2016;
U.S. Prov. Ser. No. 62/275,241 filed Jan. 6, 2016;
U.S. Prov. Ser. No. 62/275,222 filed Jan. 5, 2016;
U.S. Prov. Ser. No. 62/259,991 filed Nov. 25, 2015;
U.S. Prov. Ser. No. 62/254,718 filed Nov. 13, 2015;
U.S. Prov. Ser. No. 62/139,754 filed Mar. 29, 2015;
U.S. Prov. Ser. No. 62/120,316 filed Feb. 24, 2015; and
U.S. Prov. Ser. No. 62/119,521 filed Feb. 23, 2015.

All of the above-referenced non-provisional, provisional and international patent applications are collectively referenced herein as "the commonly assigned incorporated applications."

FIELD

This patent specification generally relates mainly to endoscopes. More particularly, some embodiments relate to portable endoscope devices that include a re-usable handle portion and a disposable or single-use cannula portion.

BACKGROUND

In the case of both rigid and flexible conventional endoscopes, the lens or fiber optic system is relatively expensive and is intended to be re-used many times. Therefore, stringent decontamination and disinfection procedures need to be carried out after each use. Disposable endoscopy is an emerging category of endoscopic instruments. In some cases, endoscopes can be made at a low enough cost for single-use applications. Disposable or single-use endoscopy lessens the risk of cross-contamination and hospital acquired diseases.

The subject matter described or claimed in this patent specification is not limited to embodiments that solve any specific disadvantages or that operate only in environments such as those described above. Rather, the above background is only provided to illustrate one exemplary technology area where some embodiments described herein may be practiced.

SUMMARY

According to some embodiments, a multi-camera, multi-spectral endoscope comprises: a single-use cannula configured for insertion in a patient; a first camera and a first light source and a second camera and a second light source, all housed at a distal end of the cannula; wherein: the first light source is configured to emit primarily light in a first wavelength range and the second light source is configured to emit light primarily in a second wavelength range that differs from the first wavelength range; the fields of view of the first camera and of the second camera and the fields of illumination of first light source and the second light source overlap at least partly such that both cameras view a same target in a patient essentially at the same time and the same target is illuminated by both light sources essentially at the same time; the first camera includes a first two-dimensional (2D) image sensor and a first color filter and the second camera includes a second 2D sensor and a second color filter that differs from the first color filter in the wavelength allowed to pass through; a processing system receiving images taken with the first camera and with the second camera and processing the images into composite images that overlay images from the first camera of selected portions of the target that have properties different from the remainder of the target on image of the target taken with the second camera and thereby highlight said selected portions of the target; and a display receiving said composite images from the processing system and displaying at least some of the received composite images.

The endoscope can further include one or more of the following features: (a) a reusable portion releasably secured to the cannula and carrying said display, wherein said display includes a third camera having a field of view that includes the distal end of the cannula, wherein said display is configured to selectively display images from the third camera system and said composite images, whereby a user can view images of the distal end of the cannula as it is being inserted in a patient and view the composite images after insertion; (b) the first camera has lower spatial resolution but higher sensitivity than the second camera; (c) the first light source emits light for fluorescent imaging and the second light source emits white light, and the first camera and the first color filter are configures to image primarily fluorescence from a target in a patient and the second camera and second color filter are configured to image primarily reflected white light from the target; (d) the first light source selectively emits light for fluorescent imaging or blue light different from that for fluoroscopic imaging and the second light source emits white light, and the first camera and the first color filter are configured to selectively image primarily fluorescence from a target in a patient or reflected blue light and the second camera and second color filter are configured to image primarily reflected white light from the target; (e) said first and second cameras and said first and second light sources selectively operate in: (i) a mode blue in which the first light source is turned ON but the second light source is turned OFF and the first camera captures a fluorescence image in which blue background is filtered out while the second camera captures a fluorescence image plus a predominantly blue background; and (ii) a mode white in which the second light source is ON but the first light source is OFF and the first camera captures a red or infrared image and the second camera captures primarily a standard white light image; (f) said processing system is configured to spatially correlate or register the images captured is said mode blue and produce first corrected and enhanced images by combining features of both; (g) said processing system is configured to spatially correlate or register the images captured is said mode white and produce second corrected and enhanced images by combining features of both; (h) said processing system is configured to combine the first corrected and enhanced images with the second corrected and enhanced images to produce said composite images; (i) the cannula includes two channels each of which is configured to serve as a fluid channel for fluid flow in or out of a patient or a working channel for surgical tools, whereby one of the channels can clear fluid or debris out of a patient during a procedure carried out with a surgical tool passing through the other channel; (j) a fluid hub at a proximal end of the cannula, wherein said cannula is configured to rotate relative to a proximal portion of the fluid hub about a longitudinal cannula axis together with a distal portion of the fluid hub; (k) a fluid hub at a proximal end of the cannula secured thereto and a reusable portion releasably secured to the fluid hub, said reusable portion including a thumb lever operatively connected to the distal end of the cannula and configured to bend the distal end of the cannula relative to a remainder of the cannula by manual operation of the thumb lever; (l) a fluid hub at a proximal end of the cannula and a reusable portion releasably secured to the fluid hub by a relative linear motion followed by a quarter turn relative rotational motion; and (m) said reusable portion includes a thumb lever a driving gear driven thereby and said fluid hub includes a driven gear meshing with the driving gear and operatively connected to the distal end of the cannula to bend the distal end in a selected direction depending on manual operation of the thumb lever.

According to some embodiments, and endoscope comprises: a single-use cannula configured for insertion in a patient; a first camera system at a distal end of the cannula; a reusable portion that is proximal to and is releasably coupled with the cannula; a display carried by the reusable portion; a second camera system carried by the display, said second camera system having a field of view that includes said distal end of the camera; whereby said display is configured to show images captured with said second camera system and showing the distal end of the cannula end environs thereof as the cannula is being inserted in a patient and to show images captured with said first camera system after insertion of the cannula in the patient.

The endoscope described in the immediately preceding paragraph ca\n further include one or more of the following features: (a) said second camera system comprises two cameras spaced from each other in a direction transverse to a longitudinal axis of the cannula and providing depth of field images of the distal end of the cannula and its environs; (b) the first camera system comprises a first camera capturing images in a first wavelength range and a second camera capturing images in a different wavelength range; and (c) further including a processing system configured to combine aspects of images captured with said first and second cameras into composite images that enhance anatomical features of medical interest.

According to some embodiments, an endoscopic method comprises: providing a single-use cannula configured for insertion in a patient; releasably attaching the cannula to a reusable portion that carries a display; concurrently capturing images of patient's organ with a first camera that is at a distal end of the cannula and captures images in a first range of wavelengths and with a second camera that also is at the distal end of the cannula but captures images in a different, second range of wavelengths; processing the images into composite images that overlay images from the first camera of selected portions of the target that have properties different from the remainder of the target on images of the target taken with the second camera and thereby highlighting said selected portions of the target; and displaying at least some of the received composite images.

The method can further include taking images of the distal end of the cannula with a third camera system carried by said display as the cannula is being inserted in a patient and selectively showing images of the distal end of the camera and its environs at said display.

As used herein, the grammatical conjunctions "and", "or" and "and/or" are all intended to indicate that one or more of the cases, object or subjects they connect may occur or be present. In this way, as used herein the term "or" in all cases indicates an "inclusive or" meaning rather than an "exclusive or" meaning.

As used herein the terms "surgical" or "surgery" refer to any physical intervention on a patient's tissues, and does not necessarily involve cutting a patient's tissues or closure of a previously sustained wound.

BRIEF DESCRIPTION OF THE DRAWINGS

To further clarify the above and other advantages and features of the subject matter of this patent specification, specific examples of embodiments thereof are illustrated in the appended drawings. It should be appreciated that these drawings depict only illustrative embodiments and are therefore not to be considered limiting of the scope of this patent specification or the appended claims. The subject matter hereof will be described and explained with additional specificity and detail through the use of the accompanying drawings in which:

FIGS. 2A and 2B are perspective views of a portable and ergonomic endoscope with disposable cannula, according to some embodiments;

DETAILED DESCRIPTION

Figure 1A:
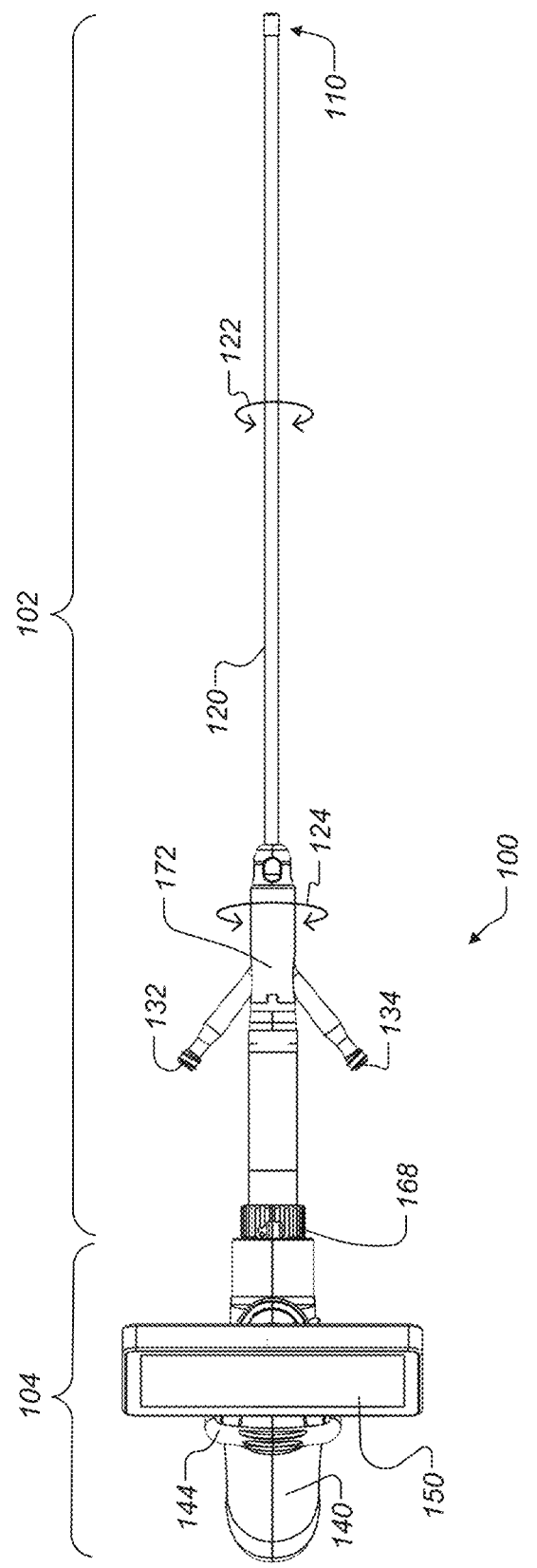
FIGS. 1A, 1B and 1C are side, top and rear views of a portable and ergonomic endoscope with disposable cannula, according to some embodiments.

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

According to some embodiments, a portable ergonomic endoscope system is described that includes an imaging system with at least two separate cameras and two separate light sources. The camera and light sources are configured to be used to simultaneously image a target object (e.g. tissue). By employing different illuminations, different filters and manipulating the spectral responses, different characteristics of the target object can be captured. According to some embodiments, a system processor can coordinate the cameras, the light sources and combine the resulting images to display to an operator an enhanced combined image of the object. According to some embodiments, the system can be configured to perform NBI (Narrow Band Imaging) imaging. According to some embodiments, the system can also be configured to perform Fluorescence Imaging.

As used herein, the term Color Filter Array (CFA) refers to a filter placed on top of a pixel to allow a certain bandwidth(s) to pass. Regular consumer cameras such as the cell phone camera uses RGB CFA. For other special applications, special CFAs can be designed.

As used herein, the term Narrow-band imaging (NBI) refers to a color imaging technique for endoscopic diagnostic medical tests, where light of specific blue and green wavelengths is used to enhance the detail of certain aspects of the surface of the mucosa. According to some embodiments, a special filter can be electronically activated by a switch in the endoscope leading to the use of ambient light preferably of wavelengths at or close to 415 nm (blue) and 540 nm (green). Because the peak light absorption of hemoglobin occurs at these wavelengths, blood vessels will appear very dark, allowing for their improved visibility and for the improved identification of other surface structures.

As used herein, the term Fluorescence Imaging (FI) refers to fluorescence imaging, sometimes using fluorescent dyes, to mark, highlight or enhance certain biological mechanisms and/or structures. Fluorescence itself, is a form of luminescence that results from matter emitting light of a certain wavelength after absorbing electromagnetic radiation. In blue light endoscopy, for example, fluorescent dyes (Hexvix) are injected in the bladder. Then blue light (around 405 nm) is used to illuminate the tissue with Hexvix which emits fluorescence of wavelength of about 610 nm. Note that with FI, the camera visualizes the fluorescence emitted from within the object, while with NBI the camera visualizes the reflections of various bandwidths of light by the object.

According to some embodiments, a novel dual camera and dual light source (DCDL) system is described for multi-spectralor multi-color imaging. Embodiments of surgical applications are disclosed with simultaneous white light, fluorescence and infrared images.

The described methodologies apply to general multi-spectral multi-band imaging. According to some embodiments, an endoscopy system is described that includes two separate camera/LED systems that are integrated into the same cannula or endoscope. A white light camera, referred to as CamW, is paired with white light LED, referred to as LightW. A fluorescence camera, referred to as CamF is paired with blue light LEDs, referred to as LightC. In this configuration, CamF is used as IR Camera when either or both LightC, LightW are off.

According to some embodiments, CamW is optimized for white light endoscopy, where strong and optimal white LEDs are used to illuminate the object, such that high image resolution can be achieved. CamF is optimized for sensitivity, because typically a fluorescence light source is weak. To maximize sensitivity and signal to noise of the CMOS sensor pixels for high quality imaging, the following are implemented:

According to some embodiments, a special color filter array (CFA) on the pixel array is used (shown in FIG. 7), such that the CMOS sensor array is sensitive to red or IR spectrum (near 600 nm or higher). According to some embodiments, to further improve sensitivity, preferably relatively large pixels (for example 2.2 um×2.2 um) are used for the CMOS sensor of CamF. In such cases, CamF preferably has lower spatial resolution than CamW pixels (for example, 1.75 um×1.75 um or 1.0 um×1.0 um) but much higher sensitivity.

Figure 1B:
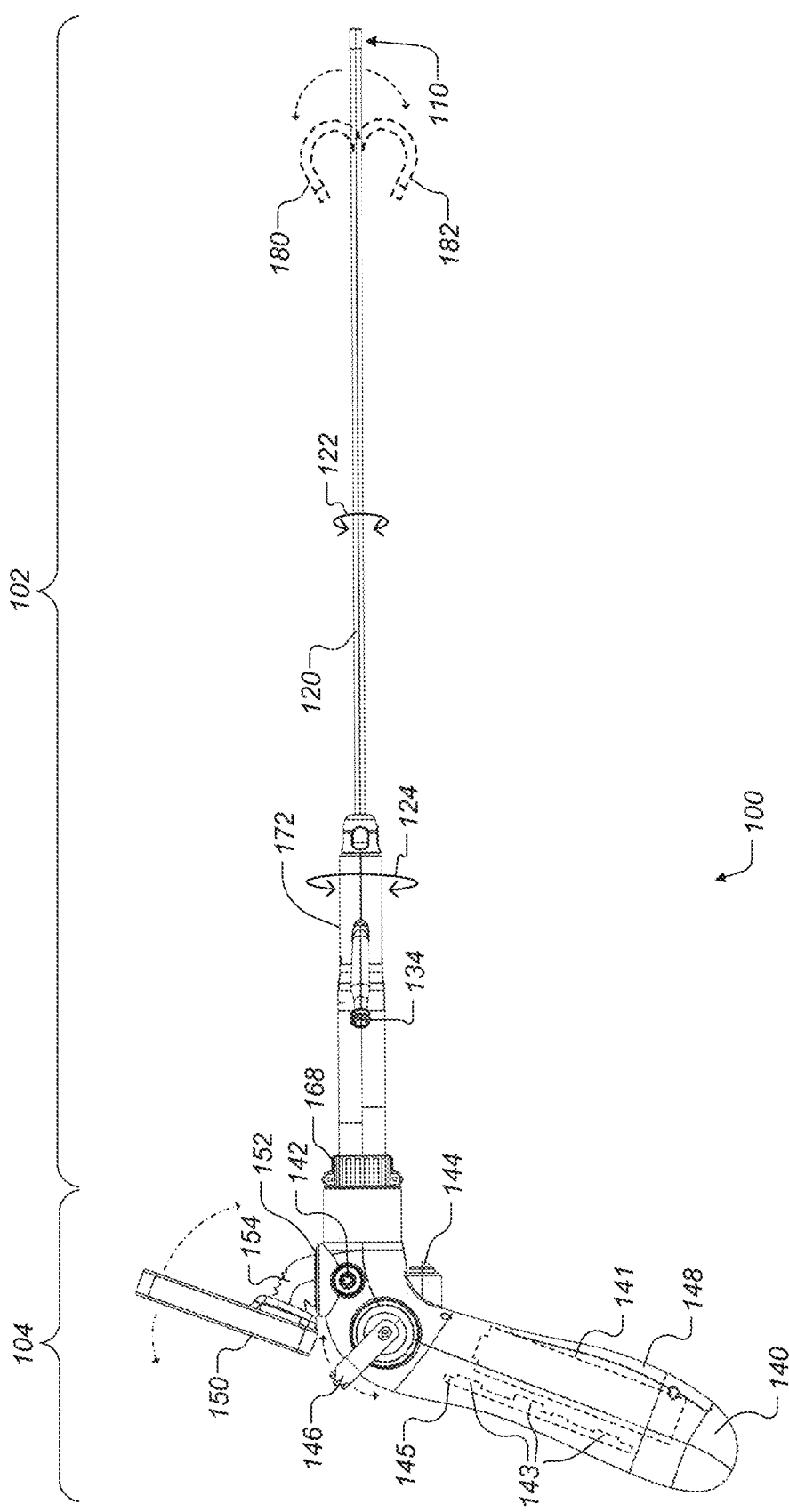
Figure 1C:
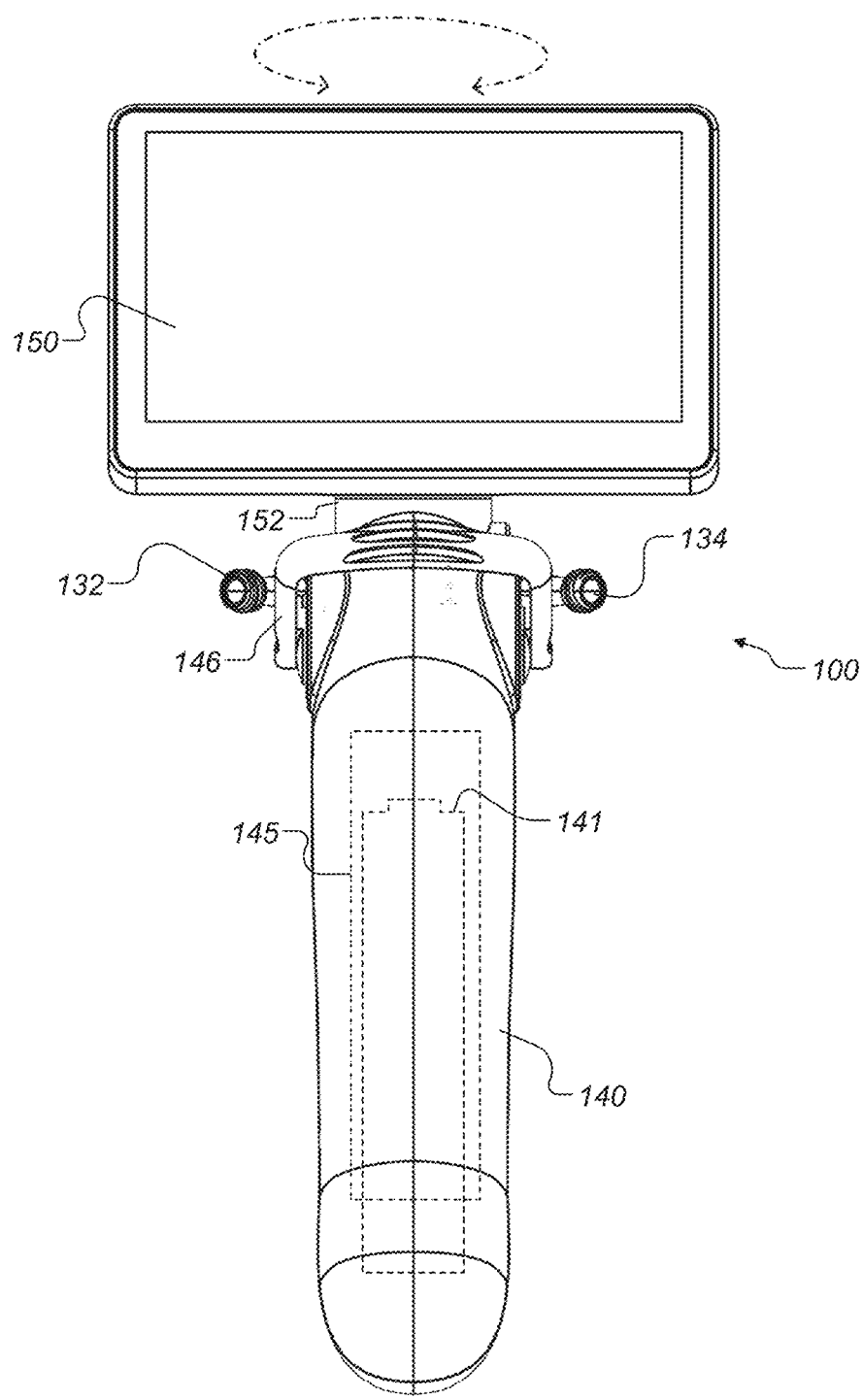

FIGS. 1A, 1B and 1C are side, top and rear views of a portable and ergonomic endoscope with disposable cannula, according to some embodiments. System 100 is adapted for easy and quick use with minimized patient discomfort and high placement accuracy. System 100 is made up of a disposable, or single-use portion 102 and a re-usable portion 104. The two portions 102 and 104 can be mated and un-mated with each other via connectors as will be shown and discussed infra in further detail. Cannula 120 has an imaging and illumination modules on its distal tip 110. An electrical cable (not shown) is positioned within the cannula and supplies control signals and power to the camera and LED illumination modules on distal tip 110 and also transmits video image data from the camera module to the hand piece 140 and display 150 for viewing by an operator. In the example shown, hand piece 140 includes two control buttons 142 and 144 which can be configured for power on/off and image capture, respectively. According to some embodiments, hand piece 140 is shaped as a pistol grip as shown and includes a rechargeable battery 141 that is accessible via battery door 148. According to some embodiments, battery 141 is an 18650-type lithium-ion battery. Also housed within handle 140 are electronics modules 143 mounted on printed circuit board (PCB) 145. Electronics modules 143 and PCB 145 are configured to carry out various processes such as video processing and capture, wi-fi transmission of data to external devices, lighting control, user interface processing, and diagnostics. Electronic modules 143 also are configured to include at least one non-volatile memory module for storing captured video and images from the camera module. According to some embodiments, display 150 can both tilt and swivel to provide optimal viewing angle for the operator. Swivel joint 152 is configured to provide swiveling of display 150 as shown by the dash dot arrow in FIG. 1C, and hinge joint 154 is configured to provide tilting of display 150 as shown by the dash dot arrows in FIG. 1B. According to some embodiments, the hinge joint is configured to allow for tilting of display in the distal direction of about 90 degrees, or nearly 90 degrees. Such tilting can be useful, for example, when give the operator an unobstructed or less obstructed view. Handle 140 also includes a thumb lever 146 that can be moved upwards or downwards as shown by the dashed arrows. Moving the thumb lever 146 upwards and downwards causes the distal tip 110 to bend upwards and downwards, respectively, as shown by dashed outlines 180 and 182, respectively. Further details of the operation of thumb lever 146 to control the steering of distal tip 110 and cannula 120 is provided in U.S. patent application Ser. No. 17/362,043 filed Jun. 29, 2021, incorporated by reference herein, which is referred to herein as "the '043 Application."

The cannula 120 is connected proximally to a fluid hub 172 including in this example two fluid ports 132 and 134. Proximal to the fluid hub is a collar 168. According to some embodiments, the collar 168 is configured to rotate so as to allow for a "plug and twist lock" style mating of portions 102 and 104, as will be shown and described in further detail infra. According to some embodiments, at least a portion of fluid hub 172, along with cannula 120 and distal tip 110, are manually rotatable relative to handle 140 along the main longitudinal axis of cannula 120, as shown by solid arrow 124. Thus, rotating the rotatable portion of hub 172 causes rotation of cannula 120 and distal tip 110 as shown by solid arrow 122. According to some embodiments, the combination of rotating cannula 120 and 110 and moving the thumb lever 146, the user can "steer" the direction of distal tip 110 as desired. According to some embodiments, the cannula 120 has a preferred working length of roughly 12 inches but shorter or longer lengths can be used depending on the medical application, and a preferred outer diameter of 5.5 to 6.5 inches but again a greater or a lesser diameter can her used depending on the medical application and developments in camera and lighting technology.

Figure 2A:
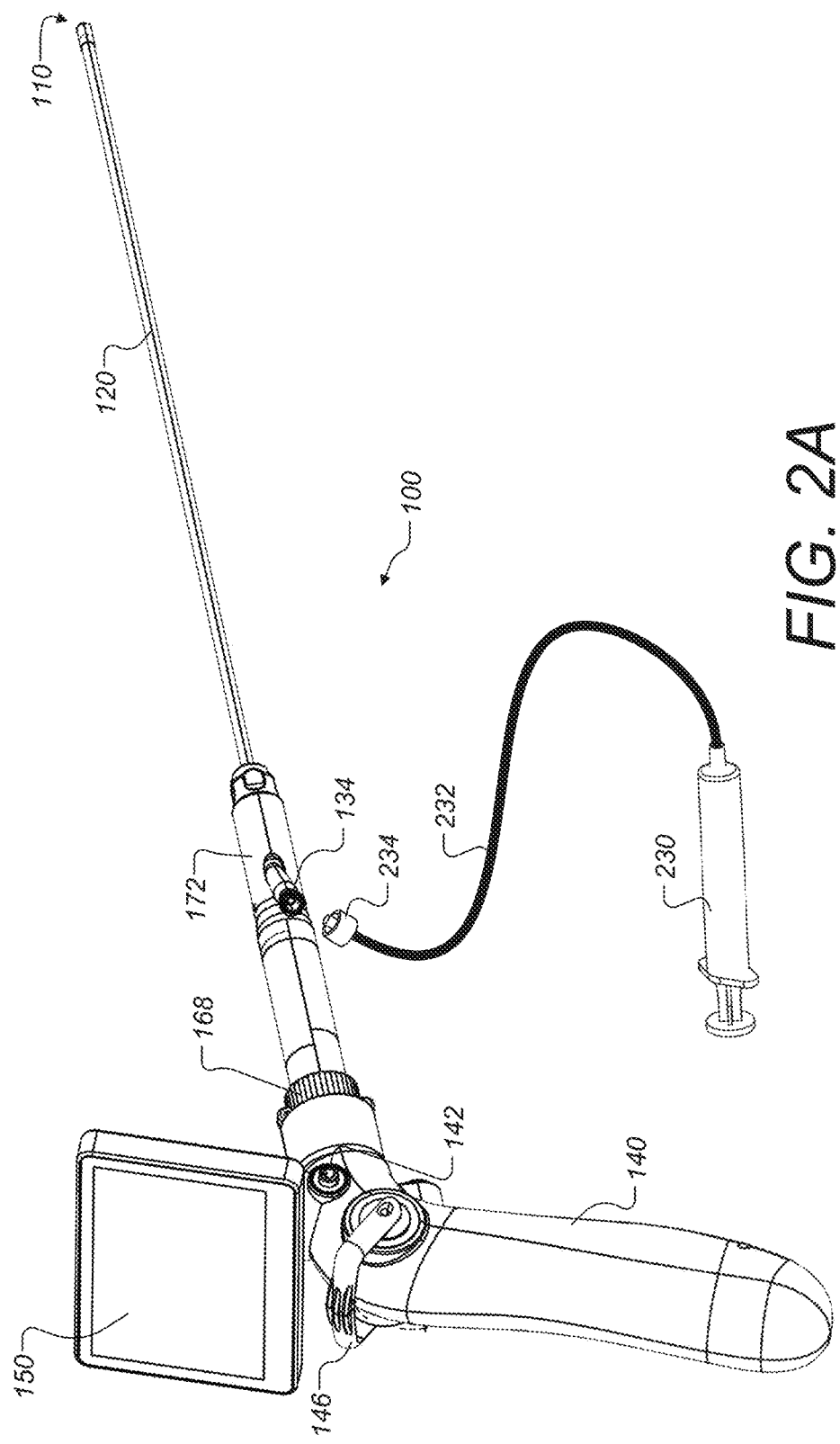

FIGS. 2A and 2B are perspective views of a portable and ergonomic endoscope with disposable cannula, according to some embodiments. FIG. 2A shows a syringe 230 used to supply fluid, such as saline, through a fluid lumen (not shown) within cannula 120 via tubing 232, connector 234 and fluid port 134. According to some embodiments the cannula 120 is semi-rigid. The cannula 120 is stiff enough so it does not collapse with longitudinal pushing and pulling forces expected in a medical procedure for which it is intended. On the other hand, cannula 120 is flexible enough such that it can bend while it passes through curved anatomy.

Figure 3A:
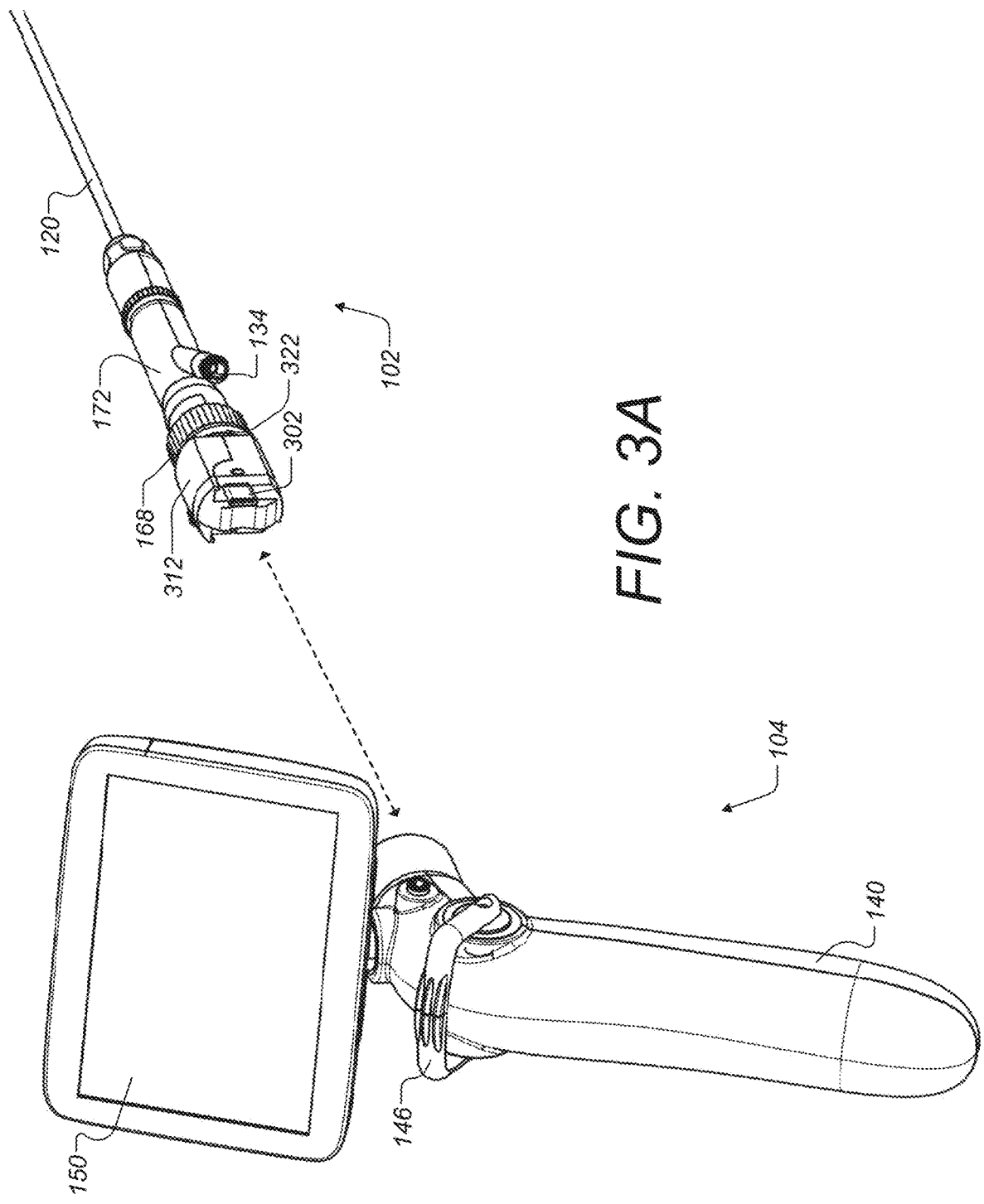
FIGS. 3A-3B are perspective views that illustrate the mating and un-mating of reusable and disposable portions of a portable and ergonomic endoscope, according to some embodiments.
Figure 3B:
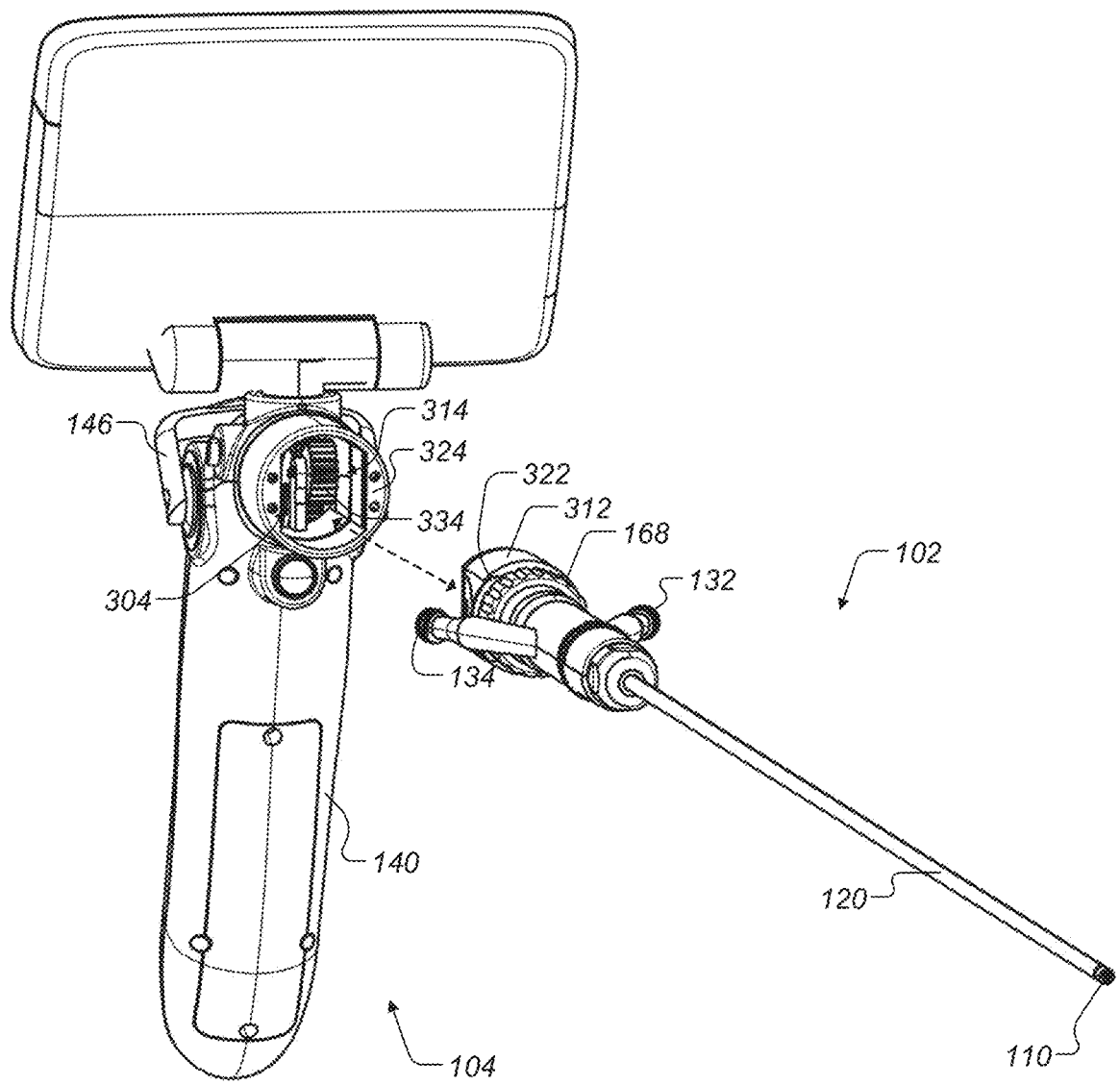

FIGS. 3A-3B are perspective views that illustrate the mating and un-mating of reusable and disposable portions of a portable and ergonomic endoscope, according to some embodiments. The portions 102 and 104 are connectable and separable via a mechanical and electrical connector. The electrical connection is made via a USB-C type plug 302 on single-use portion 102 (visible in FIG. 3A) and USB-C type receptacle 304 on multiple use portion 104 (FIG. 3B). The mechanical connection includes both a structural connection to fixedly attach portions 102 and 104 as well as a steering connection, through which steering input from the steering structure in the re-usable portion 104 can be relayed to the steering components in the single-use portion 102. The structural connection, in this example, includes a male rounded portion 312 on single-use portion 102 that is shaped to fit snugly into a female socket 314 on multiple-use portion 104. The structural connection also includes a twist lock type mechanism wherein a male portion 322 can be inserted past a female opening 324 and then locked by twisting the male portion 322 approximately one quarter turn (90 degrees). The twisting action can be applied manually via textured or knurled ring collar 168. In this way, the connection can be configured as a "plug and twist" type connection. The steering connection is provided by meshing the transmission gear 334 on the multiple-use portion 104 with the passive gear 332 on the single-use portion 102.

Figure 4A:
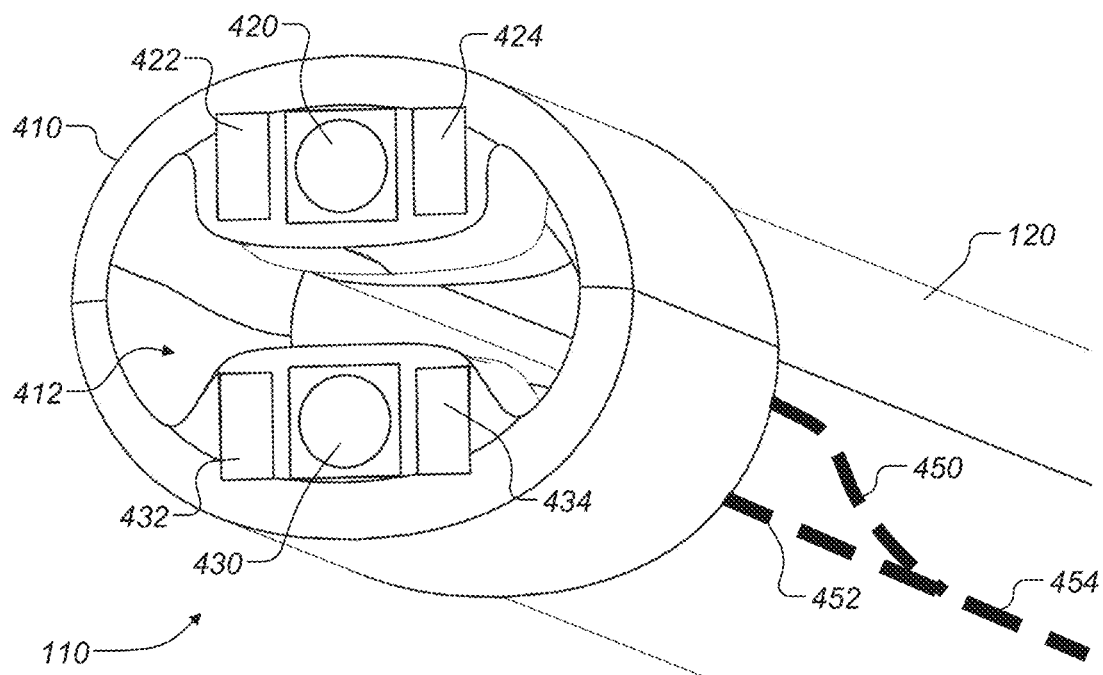
FIGS. 4A and 4B are a perspective and a schematic view of a distal tip including multiple camera and lighting modules used with a portable and ergonomic endoscope, according to some embodiments.
Figure 4B:
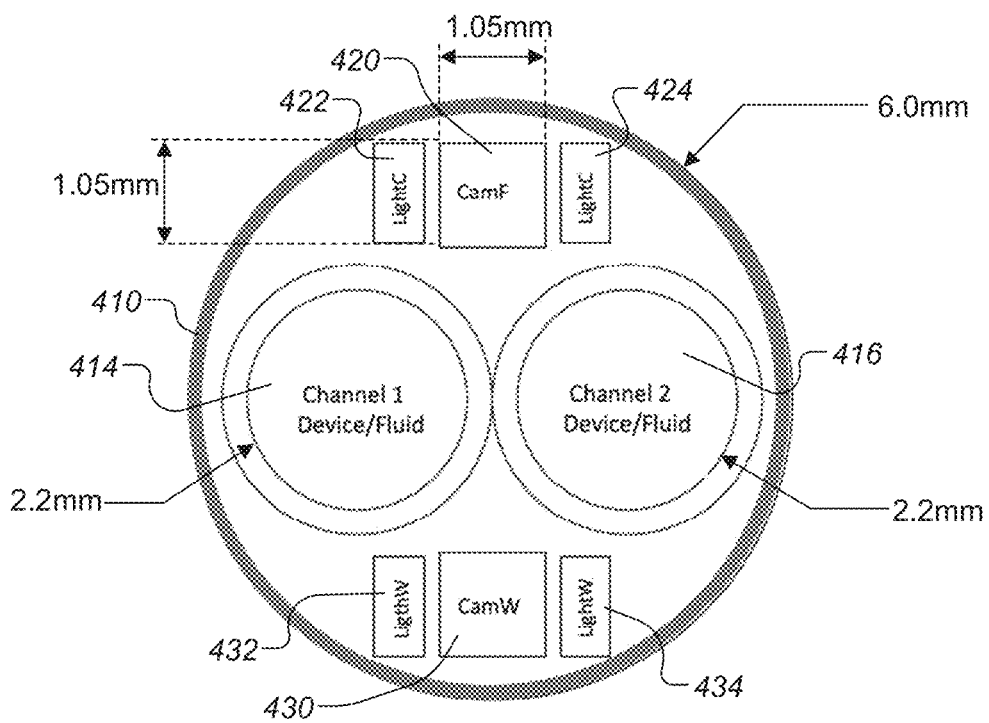

FIGS. 4A and 4B are a perspective and schematic view of a distal tip including multiple camera and lighting modules used with a portable and ergonomic endoscope, according to some embodiments. In FIG. 4A, the distal tip 110 is shown attached to the distal end of cannula 120. According to some embodiments, tip 110 includes a housing piece 410 that is molded separately from and bonded to the distal end of cannula 120. Housed within housing 410 are two camera modules: CamF module 420 and CamW module 430. Each of the CamF 420 and CamW 430 modules includes a lens and sensor. The sensors for each CamF 420 and CamW 430 include a color sensor, color filter array, and electronics and circuitry as will be described in further detail, infra. On either side of CamF module 420 are two blue LEDs 422 and 424 configured to emit excitation light suitable for fluorescence endoscopy. In some examples, the blue LEDs 422 and 424 are configured to emit light at about 410 nm (violet-blue). On either side of CamW module 430 are two white LEDs 430 and 434 configured to emit white light suitable for visible white light endoscopy. Also shown in FIG. 4A is port 412 that is configured to provide fluid (flowing either into or out of the patient) and/or provide an opening through which a tool or other device can pass (e.g. a needle). Note that although FIG. 4A shows a total of four LEDs (two white and two blue), in general, other numbers of LEDs may be provided according to factors such as desired lighting quality, endoscope size, and LED characteristics such as size and brightness. In some embodiments three or fewer LEDs can be provided and in some embodiments 10 or more LEDs can be provided. Furthermore, the number of white and blue LEDs does not have to be equal, but also will depend on various factors. The LED set can be 3, 4 or more. Other light sources can be substituted, such as optic fibers that deliver light generated elsewhere.

In FIG. 4B, the example shown includes two separate device/fluid channels 414 and 416. In this case, both have an inner diameter of 2.2 mm. According to some embodiments, channel 414 can be connected to fluid port 134 (shown in FIG. 1A) while channel 416 is connected to fluid port 132 (also shown in FIG. 1A). According to some embodiments, to boost sensitivity to fluorescence the CMOS sensor of CamF 420 is configured with larger pixels than CamW 430. For example, the CamF pixels can be 2.2 um×2.2 um arranged in a 400×400 matrix size, while the CamW pixels are 1.0 um×1.0 um or 1.75 um×1.75 um and arranged in higher spatial resolution matrix size. Because white LEDs tend to be relatively strong, the CamW 430 module can include a CMOS sensor with smaller pixels, such as 1.75 um×1.75 um or 1 um×1 um, so higher spatial resolutions can be achieved with up to 720×720 matrix size.

Figure 7:
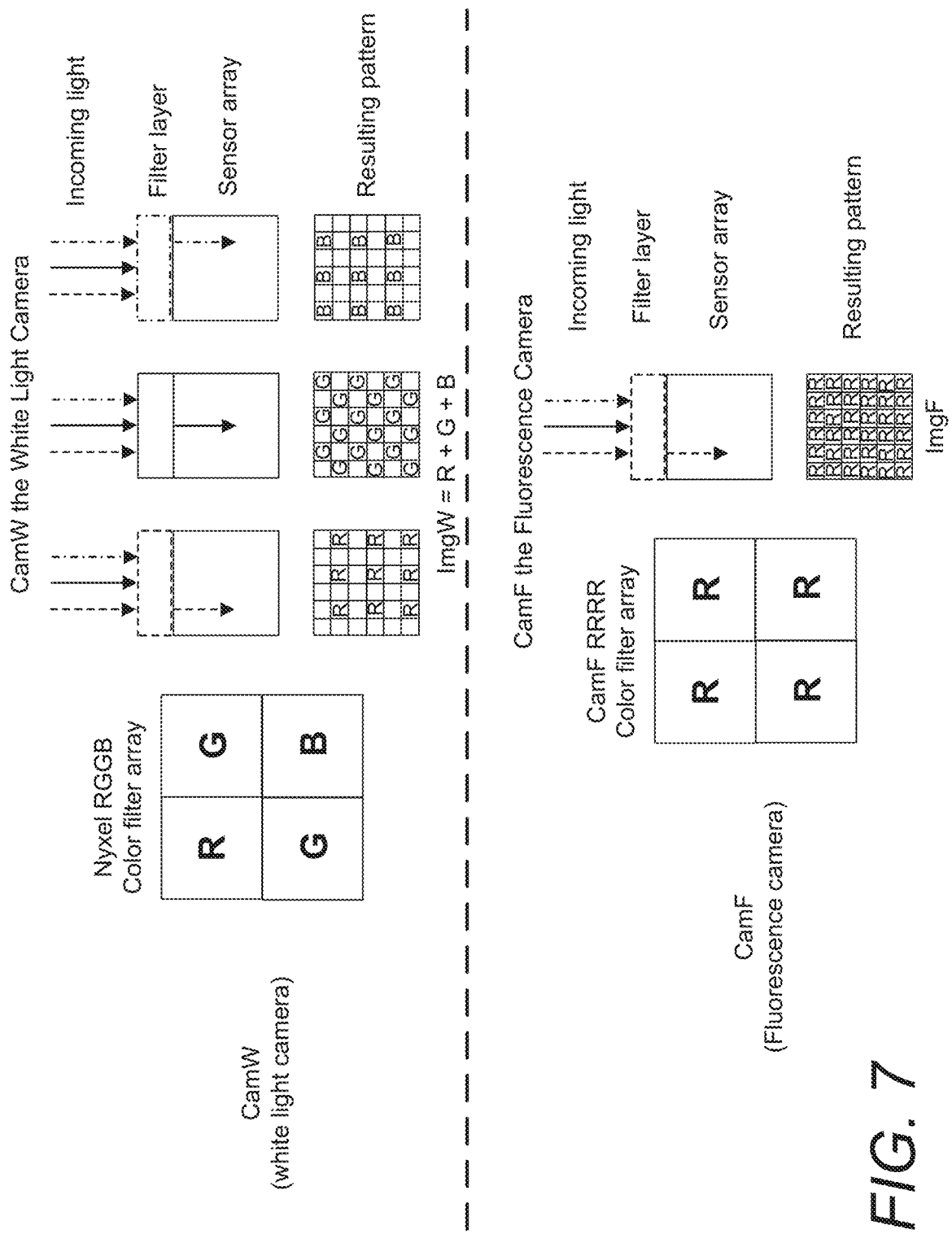
FIG. 7 is a diagram illustrating possible color filter array configurations for a dual camera dual light source system for multi-spectral imaging and surgical applications, according to some embodiments.

According to some embodiments, CamF 420 is used for blue light endoscopy, with partial CFA. An example is shown in FIG. 7 where only R Filters are used so that blue light and green light are filtered out and the majority of light that reaches the sensor is red. According to some embodiments, an IR camera is used as CamF.

Figure 5:
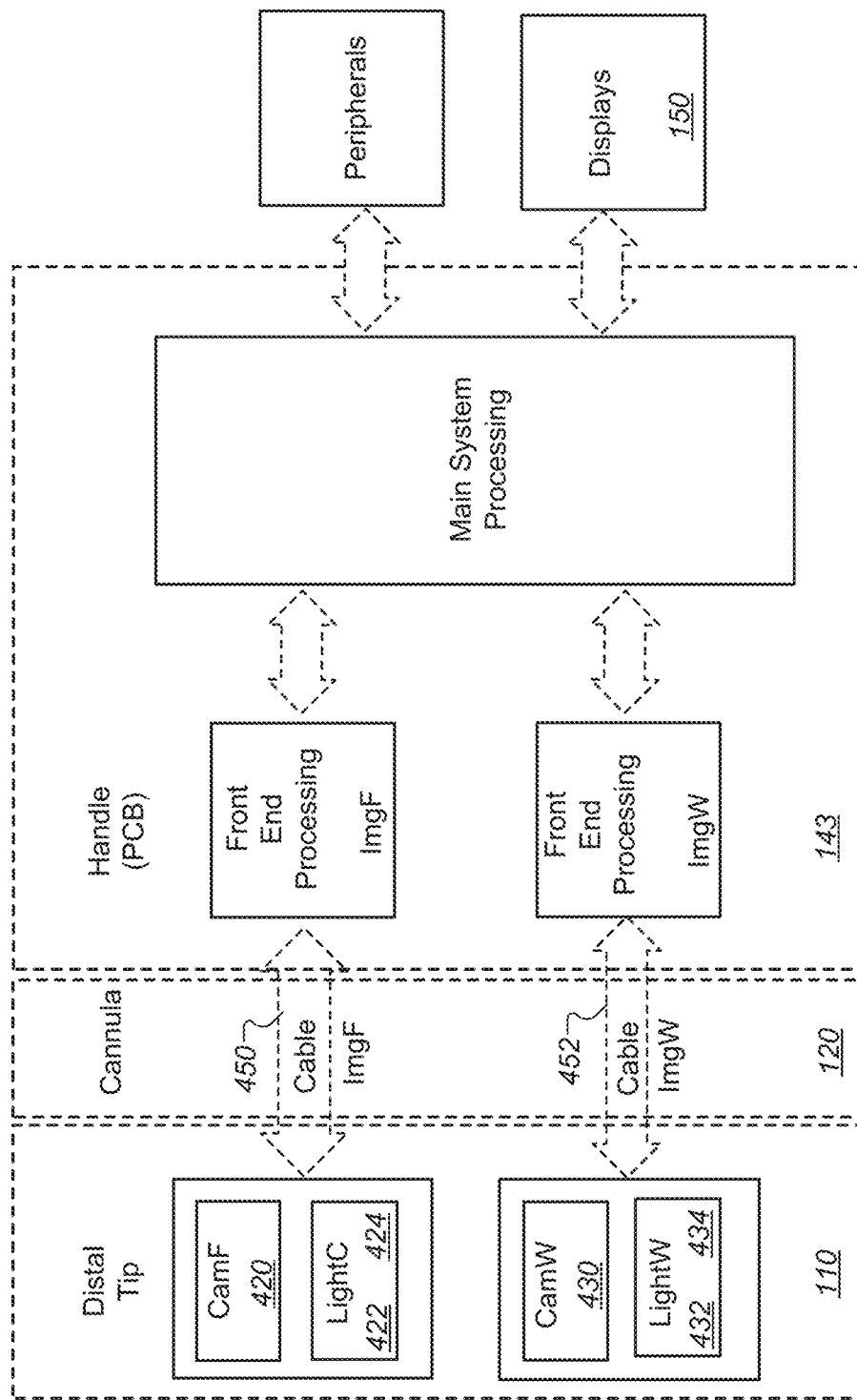
FIG. 5 is a schematic diagram of a dual camera dual light source system for multi-spectral imaging and surgical applications, according to some embodiments.

FIG. 5 is a schematic diagram of a dual camera dual light source system for multi-spectral imaging and surgical applications, according to some embodiments. As shown the distal tip 110 includes the camera and lighting modules, namely CamF, LightC, CamW and LightW. CamF camera 420 is configured for capturing images of a particular color or bandwidth, such as fluorescence with a narrow band centered around 610 nm. Filters for CamF 420 are designed to block incoming light at other wavelengths, for example by using a specially designed CFA array. CamF can be used for either NBI or FI depending on the particular application. LightC light source (422 and 424) for CamF 420, can be the excitation light in case of fluorescence imaging or simply blue or green light in the case of NBI. LEDs or special light sources can be used. According to some embodiments, CamW 430 is regular white light camera such as the camera of a cell phone. A typical RGB CFA can be used and in addition an IR filter can also be used. Typically an IR filter that filters out 50% of wavelength above 650 nm can be used. LightW (432 and 434), the light source for CamW, can be LED lights with various color tones close to white day light. The cannula 120 includes cables 450 and 452. ImgF refers to the image captured by CamF, and may be fluorescence or, in the case of NBI, reflections of green or blue lights. ImgW refers to the image captured by CamW, which maybe fluorescence or, in the case of NBI, reflections of green or blue lights.

Because the endoscope has two cameras that can operate at the same time and with different combination of lighting such as LightC, LightW (or another light band) the system takes advantage of having two "eyes" looking at the same target but seeing different aspects of the target at the same time and thus extracting more information from or about the objet and targets. For example, when blue light is on, CamF would see mostly fluorescent emission by CamW sees at the same time reflection (that can be very strong) of LightC from the object and a little bit of fluorescence. As the two cameras are in sync and also spatially registered relative to each other, composite information of different kinds is delivered to the user to improve the clinical experience over the case of seeing only one of the two kinds of information about the object or target.

According to some embodiments, Nyxel technology can be used which has been developed by OmniVision. Nyxel pixels can be used for CamF 420 and have significantly improved pixel sensitivity especially with sensitivity to red and near infrared bandwidth. This is particularly useful for detecting fluorescence around 610 nm.

In electronics modules 143, front end processing and main system processing is performed. According to some embodiments, the images are combined for display on display 150.

Figure 6:
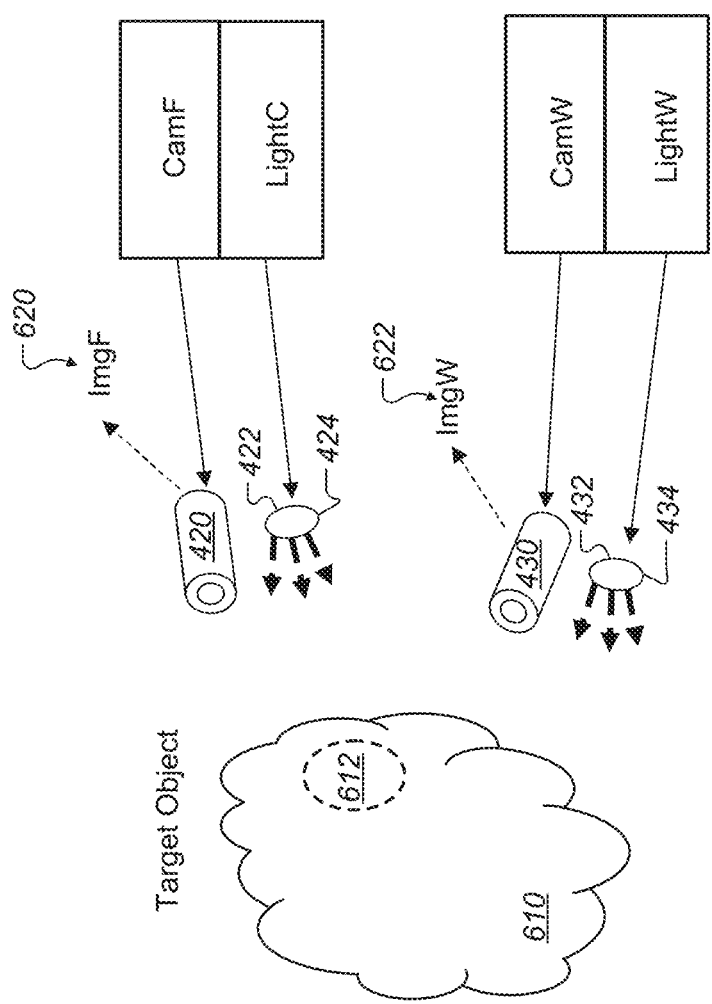
FIG. 6 is a conceptual diagram illustrating design aspects of a dual camera dual light source system for multi-spectral imaging and surgical applications, according to some embodiments.

FIG. 6 is a conceptual diagram illustrating design aspects of a dual camera dual light source system for multi-spectral imaging and surgical applications, according to some embodiments. In general, it is desirable to obtain multi-color or multi-spectral images of target objects such as human tissue. Typically, visible light images of the object plus images obtained by other color bands are used to better characterize the target tissue and shape. Two cameras (Cam F, CamW) are associated two light sources (LightC, LightW). CamF is an optical camera that is sensitive to certain color band, for example Red and IR. The output of CamF is ImgF. LightC is a light source (band C), other than white light. In Dual Band Imaging (DBI), LightC can be green or blue. In fluorescence imaging it can also be a light source that excites the object to fluorescence color. CamW is an optical camera that is sensitive to certain color band (B), for example the white light. The output of CamW is ImgW. LightW is a light source that emits certain color band B, for example the white light.

FIG. 7 is a diagram illustrating possible color filter array configurations for a dual camera dual light source system for multi-spectral imaging and surgical applications, according to some embodiments. According to some embodiments, CamF uses a Nyxel pixel (from Omnivision) and a "Red Only" filter array, the CamF RRRR filter. This arrangement allows for red and/or IR band to pass while filtering out the background blue and green light.

The CamF can achieve four times the resolution for red compared to that of Nyxel CFA or Old CFA, because one out of four pixels in Nyxel or Old CFA arrangements are used to capture red color. On the other hand, every pixel in CamF arrangement in FIG. 7 is used to capture red color.

Figure 8:
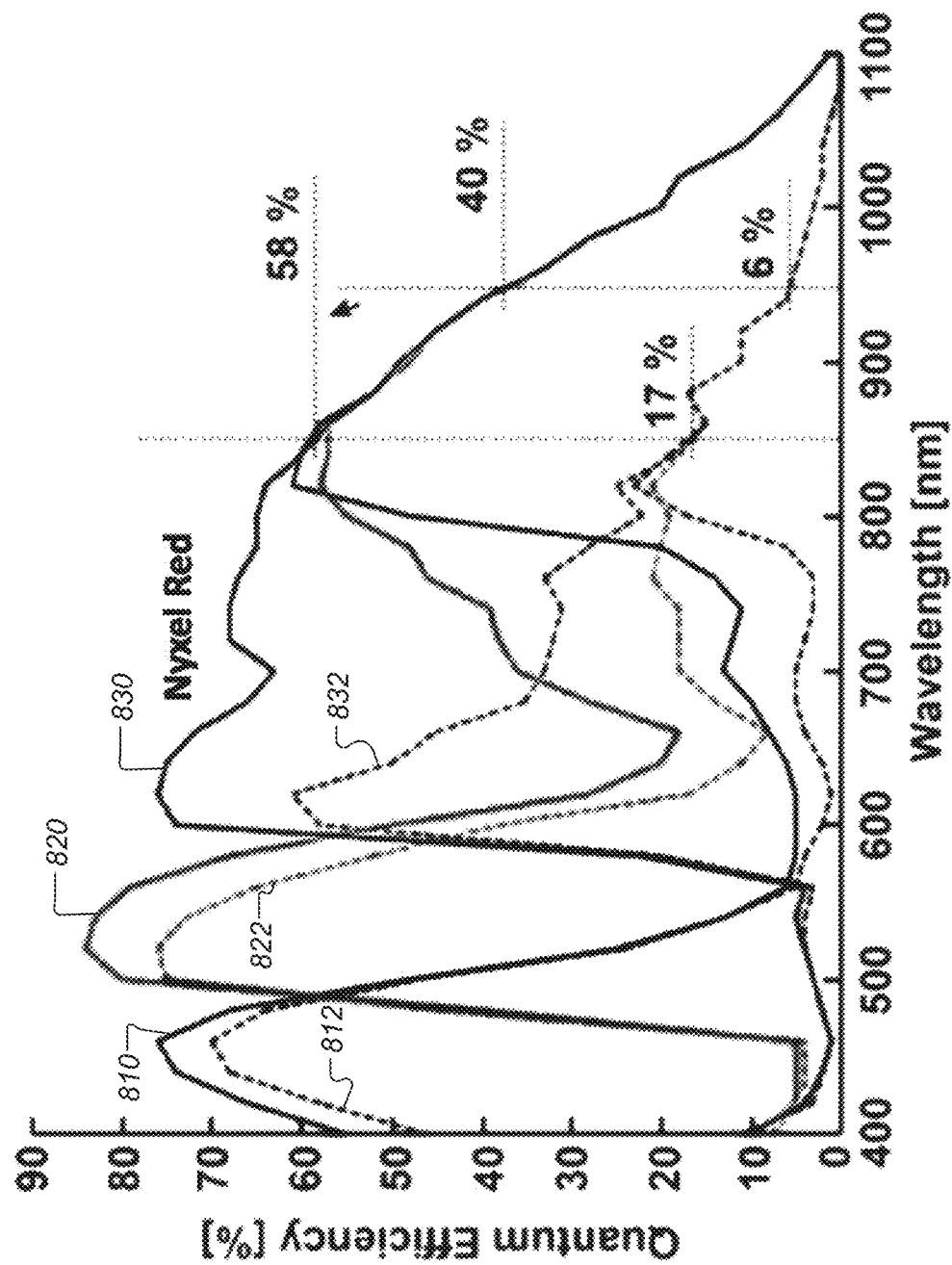
FIG. 8 is a plot showing quantum efficiency versus wavelength for Nyxel and conventional pixels.

FIG. 8 is a plot showing quantum efficiency versus wavelength for Nyxel and conventional pixels. In this figure, quantum efficiency is shown the new sensor developed by OminiVision, the Nyxel pixel. Curve 810 is a Nyxel blue pixel. Curve 812 is a conventional blue pixel. Curve 820 is a Nyxel green pixel. Curve 822 is a conventions green pixel. Curve 830 is a Nyxel red pixel. Curve 832 is conventional red pixel. It can be seen especially curves 830 and 832 that the Nyxel red pixel has a significantly higher sensitivity to the red or IR band than the regular conventional red pixel.

Figure 9:
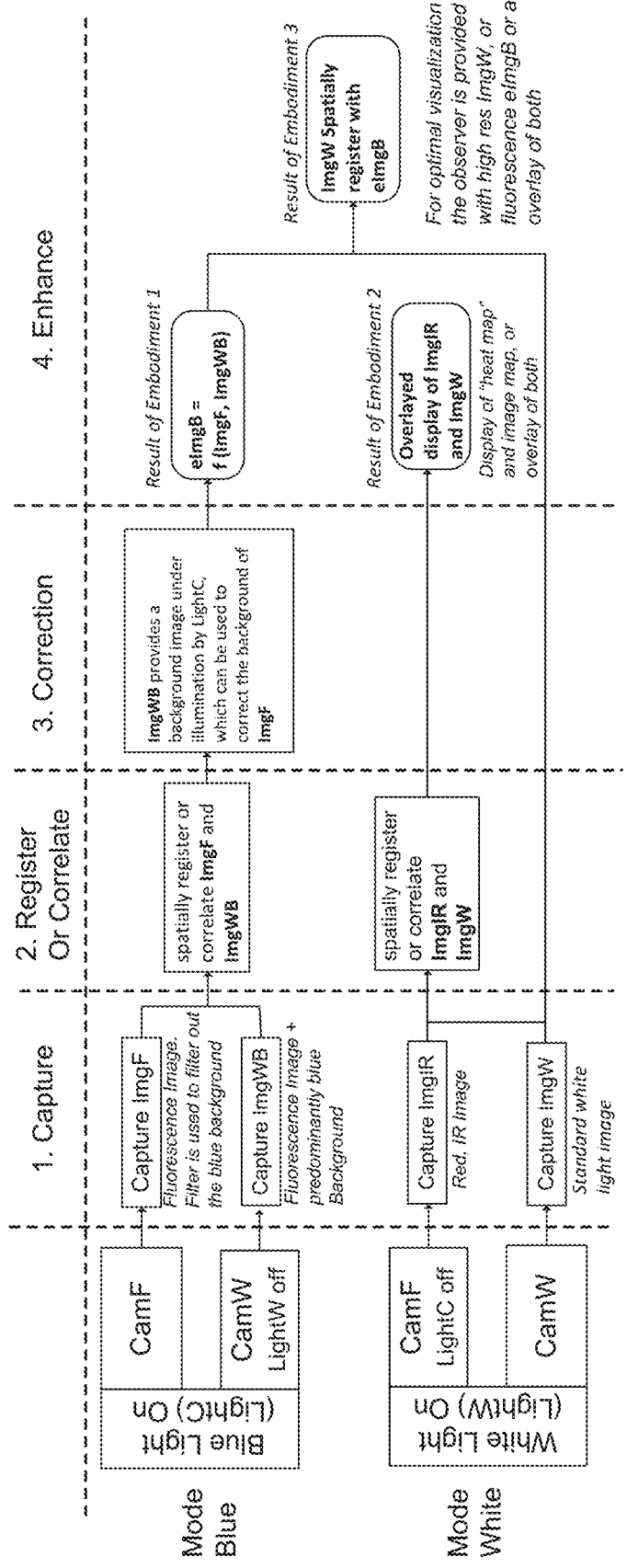
FIG. 9 is a diagram illustrating further aspects of combining multi-band image data from a dual camera dual light source system, according to some embodiments.

FIG. 9 is a diagram illustrating further aspects of combining multi-band image data from a dual camera dual light source system, according to some embodiments. With the availability of global shutter capability CamF, CamW can capture image frames under different combinations of LightC and LightW being turned "on" or "off." In "Surgical Embodiment 1" with the LightC (blue light) "on" but the LightW "off", the resulting captured images are ImgF from CamF and ImgWB from CamW. ImgF and ImgWB are spatially registered or correlated. This can be done due to the short time lag (or completely in sync when both cameras capture simultaneously) between images captured by the different cameras. ImgWB provides a background image under illumination by LightC, which can be used to correct the background of ImgF. The ImgF data combined with ImgWB when only LightC is on produces "eImgB."

In the case of Blue Light Endoscopy, ImgF has low signal to noise ratio (due to weak fluorescence signal), therefore CMOS sensor with high signal to noise pixels is used. On the other hand, ImgW has high signal to noise (due to strong white light), therefore CMOS sensor with smaller pixels can be used to boost spatial resolution.

In "Surgical Embodiment 2" CamF is used to capture ImgIR with the LightC "off." CamW captures the standard white light image with LightW "on." In this case ImgIR provides a "heat map" of the target; it is useful when energy devices such as laser or RF are used for tissue modification. ImgIR can alert users of hot or cold spots. The ImgIR and ImgW data can be spatially registered or correlated, again, due to the short time lag (or no time lag) between images captured by the different cameras. ImgIR and ImgW can also be combined or overlayed to provide a precise location of the hot and cold spots. That is, the hot and cold spots can be viewed in the context of an ordinary standard white light image to provide the viewer with locational context of the hot and cold spots.

In "Surgical Embodiment 3" ImgW is combined with eImgB. By combining embodiments 1 and 2, the high quality eImgB data is spatially registered with the white light image ImgW. The observer is provided with high res ImgW, or fluorescence eImgB or an overlay of both. According to some embodiments, surgeons can employ images available to better visualize their targets. The fluorescence Image eImgB, the white light image ImgW and IR Image ImgIR and seamlessly switch between different visualization modes.

According to a fourth "Embodiment 4" (not shown in FIG. 9) with accumulation of clinical cases, artificial intelligence algorithm (or machine learning) can be designed for automated diagnosis.

Figure 10:
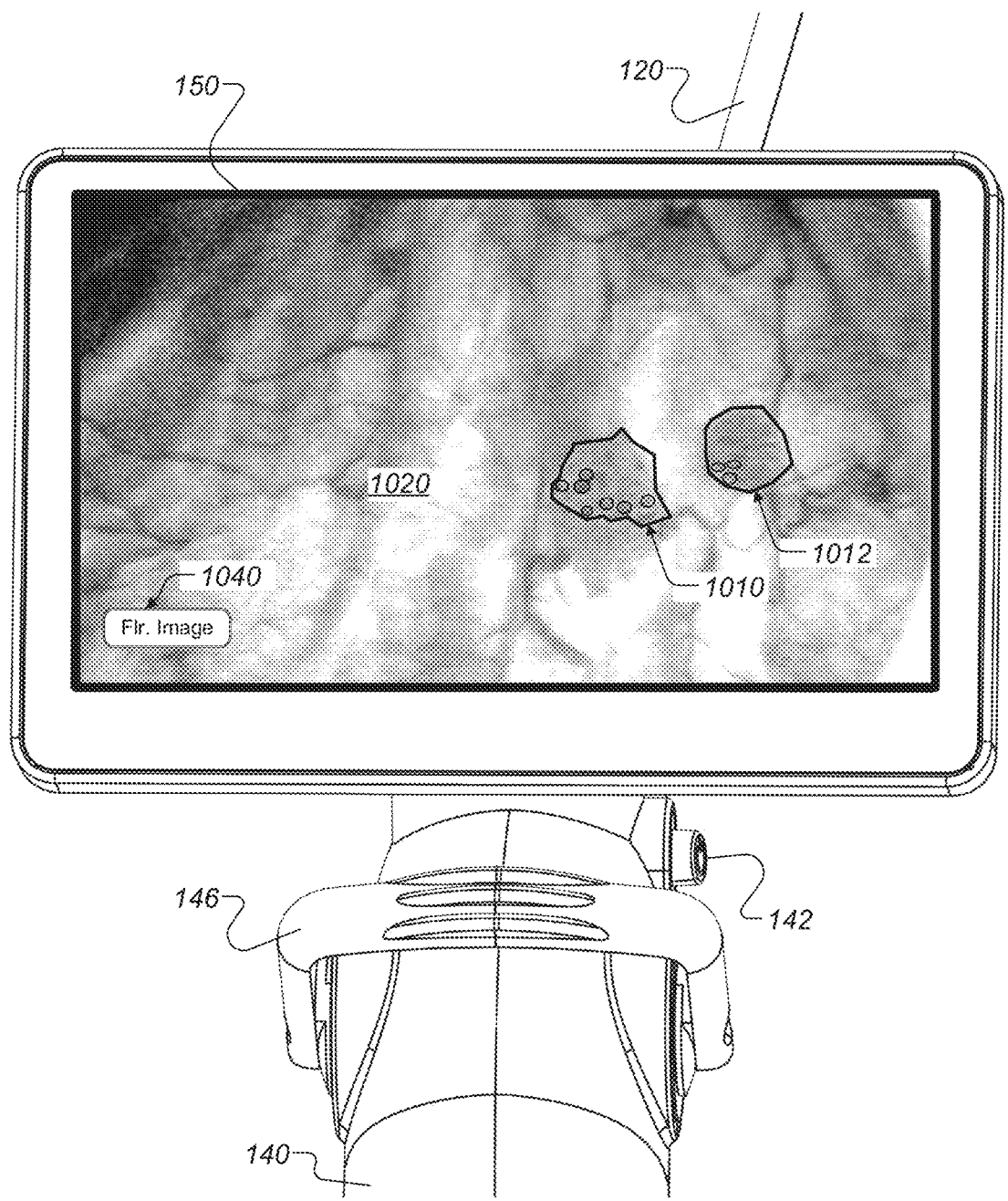
FIG. 10 is a perspective view in which a combined, spatially registered image displayed to a user on an endoscopy system, according to some embodiments.

FIG. 10 is a perspective view in which a combined, spatially registered image is displayed to a user on an endoscopy system, according to some embodiments. In the displayed view, the ordinary white light image (ImgW) 1020 is displayed over most of the display screen 150. The example shown is "Embodiment 3" shown in FIG. 9, where the eImgB image is combined and spatially registered with the standard white color image (ImgW). In this case the regions 1010 and 1012 are obtained from the eImgB data and clearly show cancerous tumors. The operator can easily view the cancerous regions 1010 and 1012 in spatial registration with the ordinary color image of the surrounding tissue. This blending or combination provides a greatly enhanced view of the target tissue. According to some embodiments, the operator can easily switch between different modes (e.g. Embodiment 1, 2 or 3) by pressing a toggle button such as button 142, button 144 (shown in FIGS. 1B and 2B), or by a soft-button 1040 on touch-sensitive display 150.

Figure 11:
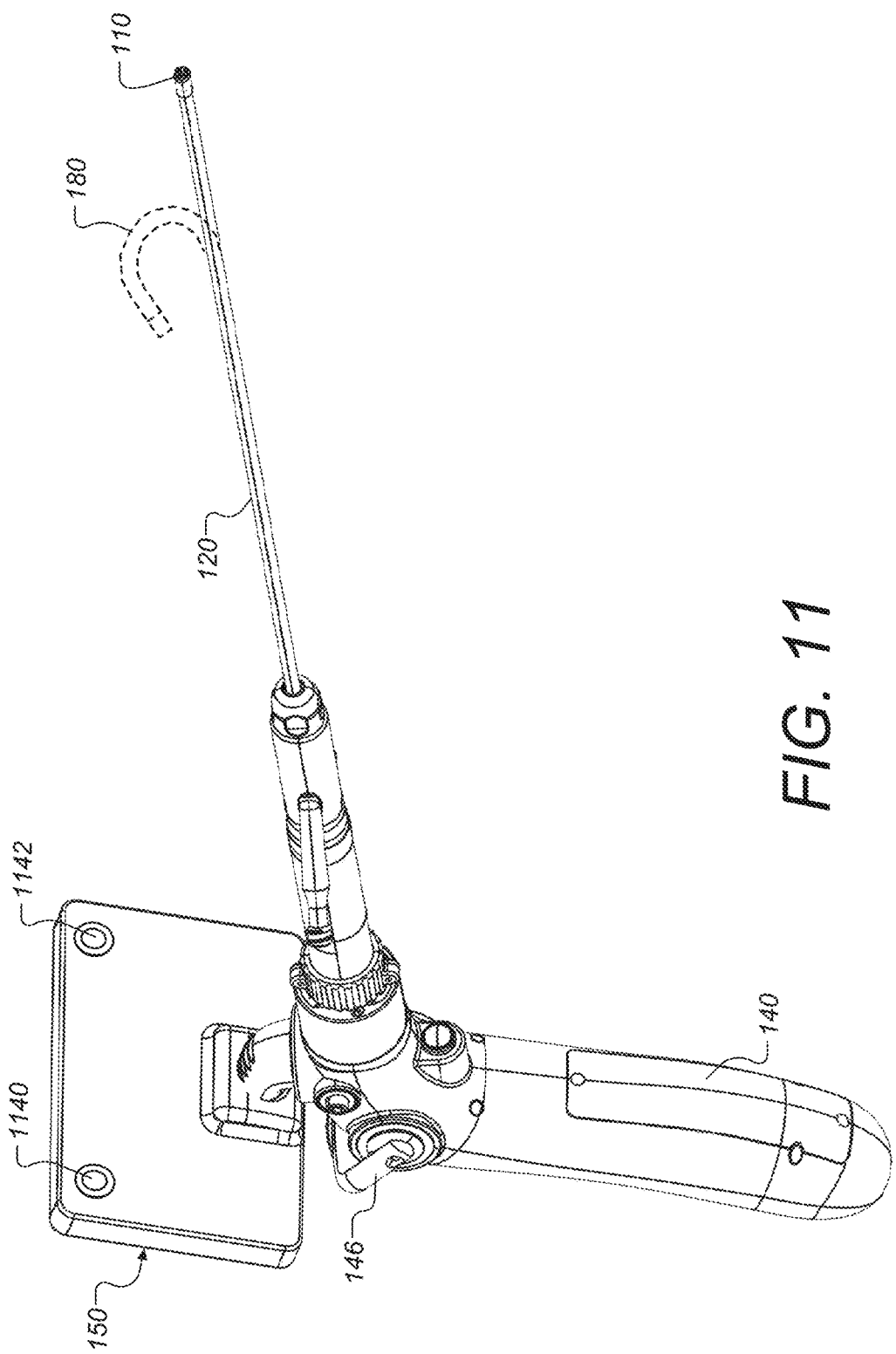
FIG. 11 is a perspective view of a endoscopy system having one or more forward facing cameras, according to some embodiments.

FIG. 11 is a perspective view of an endoscopy system having one or more forward facing cameras, according to some embodiments. The example shown has two forward (distally) facing cameras 1140 and 1142. The forward facing cameras allow the operator to see precisely where the distal tip is located, without having to move the screen out of the way. During a surgical procedure, especially immediately prior to or during initial insertion of the tip 110, the operator's view can be primary focused on the display screen 150. With forward facing cameras, 1140 and 1142, the precise location of the distal tip and its surroundings can be viewed on the display 150. Image enhancements such as artificially providing a depth of field may be beneficial in some procedures. The two cameras or other means (e.g. LIDAR imaging) may be used to simulate a depth of field centered on the distal tip to enhance usability.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What it claimed is:

1. A multi-camera, multi-spectral endoscope comprising:
a single-use cannula configured for insertion in a patient;
a first forward-looking camera having a first field of view and a first light source having a first field of illumination and a second forward-looking camera having a second field of view and a second light source having a second field of illumination, all housed at a distal end of the cannula and selectively operating in a first mode in which:
the first light source is configured to emit primarily light in a first wavelength range and the second light source is configured to emit light primarily in a second wavelength range that differs from the first wavelength range;
the fields of view of the first camera and of the second camera and the fields of illumination of first light source and the second light source overlap at least partly such that both cameras view a same target in a patient at the same time;
the first camera includes a first two-dimensional (2D) image sensor and a first color filter and the second camera includes a second 2D sensor and a second color filter that differs from the first color filter in wavelength ranges allowed to pass through;
a processing system receiving images taken at the same time with the first camera and with the second camera and processing the images into first composite images that overlay images from the first camera of selected portions of the target that have properties different from the remainder of the target on image of the target taken with the second camera and thereby highlight said selected portions of the target; and a display receiving said composite images from the processing system and displaying at least some of the received composite images.

2. The endoscope of claim 1, further including a reusable portion releasably secured to the cannula mechanically and electrically and carrying said display, wherein said display includes a third camera system having a third field of view that includes the distal end of the cannula, wherein said display is configured to selectively display images from the third camera system and said composite images, whereby a user can view images of the distal end of the cannula and the target and view the composite images after insertion.

3. The endoscope of claim 1, in which the first camera has lower spatial resolution but higher sensitivity than the second camera.

4. The endoscope of claims 1, in which the first light source emits light for fluorescence stimulation and the second light source emits white light, and the first camera and the first color filter are configured to image primarily fluorescence from the target and the second camera and second color filter are configured to image primarily reflected white light from the target.

5. The endoscope of claim 1, in which the first light source selectively emits light for fluorescent imaging or blue light different from that for fluoroscopic imaging and the second light source emits white light, and the first camera and the first color filter are configured to selectively image primarily fluorescence from a target in a patient or reflected blue light and the second camera and second color filter are configured to image primarily reflected white light from the target.

6. The endoscope of claim 1, in which said first and second cameras and said first and second light sources additionally selectively operate in:
 a. a mode blue in which the first light source is turned ON but the second light source is turned OFF and the first camera captures a fluorescence image in which blue background is filtered out while the second camera captures a fluorescence image plus a predominantly blue background; and
 b. a mode white in which the second light source is ON but the first light source is OFF and the first camera captures a red or infrared image and the second camera captures primarily a standard white light image.

7. The endoscope of claim 6, in which said processing system is configured to spatially correlate or register the images captured is said mode blue and produce first corrected and enhanced images by combining features of both.

8. The endoscope of claim 7, in which said processing system is configured to spatially correlate or register the images captured is said mode white and produce second corrected and enhanced images by combining features of both.

9. The endoscope of claim 8, in which said processing system is configured to combine the first corrected and enhanced images with the second corrected and enhanced images to produce second composite images.

10. The endoscope of claim 1, in which the cannula includes two channels each of which is configured to serve as a fluid channel for fluid flow in or out of a patient or a working channel for surgical tools, whereby one of the channels can clear fluid or debris out of a patient during a procedure carried out with a surgical tool passing through the other channel.

11. The endoscope of claim 1, further including a fluid hub at a proximal end of the cannula, wherein said cannula is configured to rotate relative to a proximal portion of the fluid hub about a longitudinal cannula axis together with a distal portion of the fluid hub.

12. The endoscope of claim 1, further including a fluid hub at a proximal end of the cannula secured thereto and a reusable portion releasably secured to the fluid hub, said reusable portion including a thumb lever operatively connected to the distal end of the cannula and configured to bend the distal end of the cannula relative to a remainder of the cannula by manual operation of the thumb lever.

13. The endoscope of claim 1, further including a fluid hub at a proximal end of the cannula and a reusable portion that releasably mounts to the fluid hub by a relative linear motion followed by a quarter turn relative rotational motion.

14. The endoscope of claim 13, in which said reusable portion includes a thumb lever and a driving gear driven thereby and said fluid hub includes a driven gear meshing with the driving gear and operatively connected to the distal end of the cannula to bend the distal end in a selected direction depending on manual operation of the thumb lever.

15. An endoscope comprising:
 a single-use cannula\configured for insertion in a patient;
 a first camera system\at a distal end of the cannula;
 a reusable portion that is proximal to and is releasably coupled with the cannula mechanically and electrically for form a hand-carried endoscope as a single unit;
 a display carried by the reusable portion;
 a display-mounted, second camera system, said second camera system having a fixed field of view that includes said distal end of the cannula and environs thereof;
 whereby said display is configured to show images captured with said second camera system and showing the distal end of the cannula and environs thereof and to show images captured with said first camera system.

16. The endoscope of claim 15, in which said second camera system comprises two cameras spaced from each other in a direction transverse to a longitudinal axis of the cannula and providing depth of field images of the distal end of the cannula and its environs.

17. The endoscope of claim 15, in which the first camera system comprises a first camera capturing images in a first wavelength range and a second camera capturing images in a different wavelength range.

18. The endoscope of claim 17, further including a processing system configured to combine aspects of images captured with said first and second cameras into composite images that enhance anatomical features of medical interest.

19. An endoscopic method comprising:
 providing a single-use cannula configured for insertion in a patient;
 releasably attaching the cannula mechanically and electrically to a reusable portion that carries a display;
 selectively operating a first forward-looking camera and a second forward-looking camera at a distal end of the cannula in a mode capturing images of a target with the first camera in a first range of wavelengths and at the same time capturing images of the target with a second camera in a different, second range of wavelengths;
 processing the images into composite images that overlay images from the first camera of selected portions of the target that have properties different from the remainder of the target on images of the target taken with the second camera to thereby highlight said selected portions of the target; and displaying at least some of the composite images at a display.

20. The method of claim 19, further including taking images of the distal end of the cannula with a display-mounted camera system and selectively showing said images of the distal end of the camera and its environs at said display.

* * * * *